United States Patent [19]

Targosz

[11] Patent Number: 4,534,212

[45] Date of Patent: Aug. 13, 1985

[54] FULLY AUTOMATIC PENETRATION HARDNESS TESTER

[75] Inventor: Thomas C. Targosz, Oak Park, Mich.

[73] Assignee: K. J. Law Engineers, Inc., Farmington Hills, Mich.

[21] Appl. No.: 509,318

[22] Filed: Jun. 30, 1983

[51] Int. Cl.$^3$ .............................................. G01N 3/44
[52] U.S. Cl. ....................................................... 73/83
[58] Field of Search ......................... 73/83, 81, 862.48

[56] References Cited

U.S. PATENT DOCUMENTS

| | | | |
|---|---|---|---|
| 3,416,367 | 12/1968 | Ernst ....................................... | 73/83 |
| 4,245,496 | 1/1981 | Napetschnig ........................... | 73/83 |
| 4,331,026 | 5/1982 | Howard et al. ......................... | 73/81 |

OTHER PUBLICATIONS

Dorf, Richard C., *Modern Control Systems*, Addison-Wesley Pub. Co., 1974, pp. 110–119.

*Primary Examiner*—John W. Caldwell, Sr.
*Assistant Examiner*—E. G. Harding, Jr.
*Attorney, Agent, or Firm*—Barnes, Kisselle, Raisch, Choate, Whittemore & Hulbert

[57] ABSTRACT

A fully automatic penetration hardness tester which includes a penetrator and clamp driven by respective serially-connected pneumatic cylinders for engaging test specimens. Pressure regulators are coupled to the respective cylinders for first applying clamping pressure against the test specimen and then applying a plurality of loads in a predetermined sequence to the clamped specimen through the penetrator, with the total clamping and penetrator pressure against the test specimen remaining constant through the test cycle. A control circuit monitors penetrator position and automatically initiates application of the next load in the test sequence when motion of the penetrator following application of the preceding load has settled such that a predetermined number of sequential position readings fall within a preselected position range. Specimen hardness is determined as a linear function of penetration depth under the various loads. An automatic calibration feature determines gain and offset of such linear function from actual and apparent hardnesses of two test specimens of known differing hardness.

17 Claims, 3 Drawing Figures

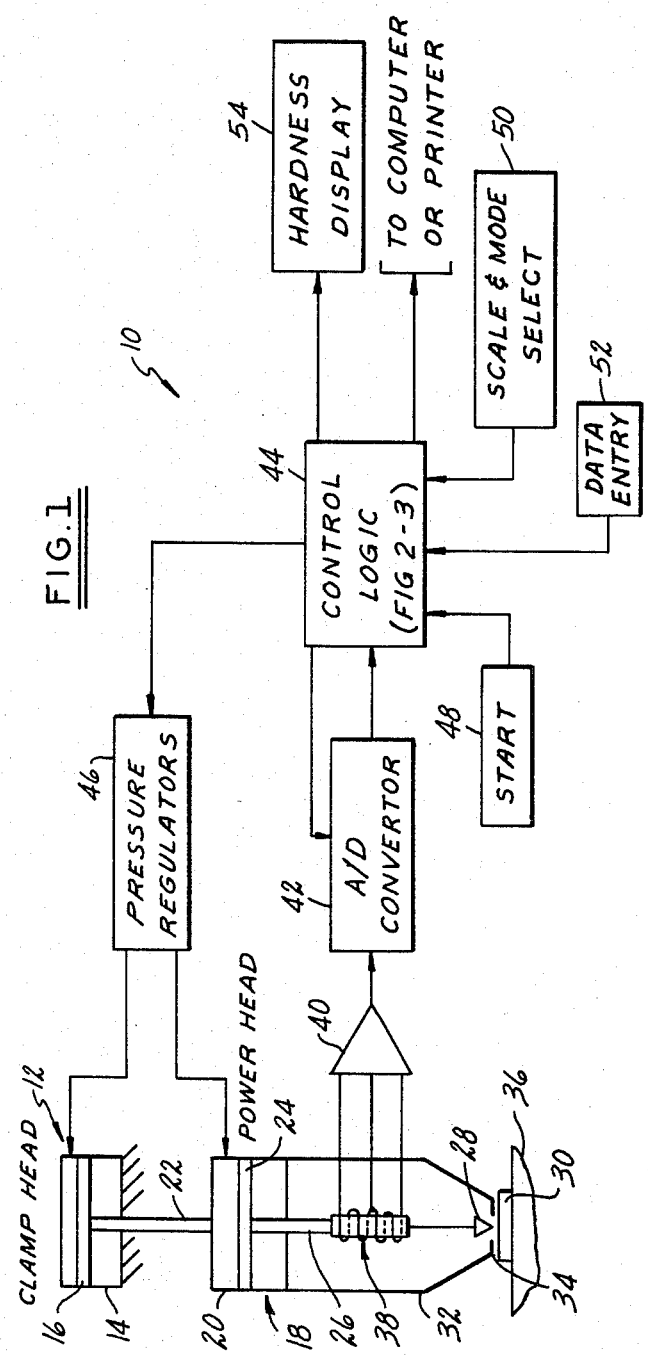
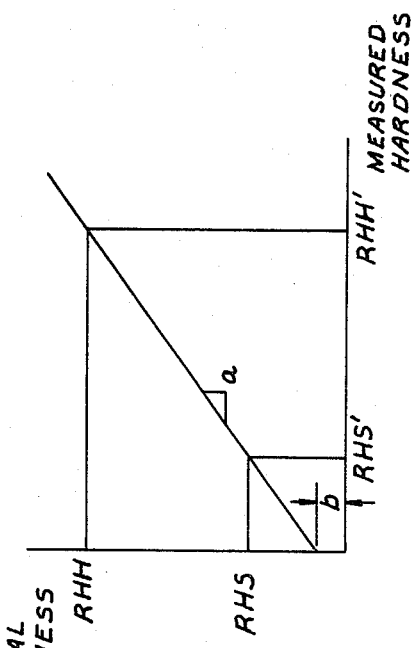

FULLY AUTOMATIC PENETRATION HARDNESS TESTER

The present invention is directed to penetration hardness testers, and more particularly to automatic hardness testers for providing a reading of specimen hardness measured in one of a plurality of selectable hardness scales.

BACKGROUND OF THE INVENTION

Penetration hardness testers are well-known in the art, and generally include a diamond- or ball-tip penetrator and means for applying minor and major loads of predetermined magnitude through the penetrator to a test specimen in successive load cycles. The minor load is first applied, and the penetrator position is noted. The major load is then applied and removed, with the minor load still applied, and penetrator position is again noted. Specimen hardness is then determined as a function of a difference in these minor-load penetrator positions.

It is important in performing such hardness tests that the penetrator load be fully applied or removed, and that the penetrator be allowed to settle in position, before noting penetrator position or advancing to the next load cycle. (It will be appreciated that the term "load cycle" is employed in the generic sense as encompassing both application and removal of a selected load.) In manual testers, this is typically accomplished by an operator by observing a dial indicator responsive to penetrator position. The U.S. Pat. No. 4,182,164 to Fohey issued Jan. 8, 1980 to the assignee hereof discloses a semi-automatic penetration hardness tester with digital readout which includes means for detecting proper application of minor and major loads, and for aborting the test sequence in the event of improper application or early removal.

Previous attempts to provide fully automated penetration hardness testing have incorporated delay circuits or timers for suspending operation for a predetermined time after a load has been applied or removed. This delay time is selected to be sufficiently long so that it can be assumed that penetrator motion has settled after each load cycle before a reading is taken of penetrator position. ASTM Specification E-18, for example, provides for a delay of several seconds after each load cycle, requiring on the order of ten seconds to complete a load sequence and obtain a hardness reading. Of course, penetrator settling time varies with material hardness, so that such automated schemes must be designed to accommodate worst-case situations, thereby necessitating substantial, often unnecessary delays. These delays present a major impediment to 100% test applications in production environments. In a laboratory environment, the requisite delays test operator patience, and often result in readjustment of the delay time and inaccurate test results Another problem extant in the art of automated hardness testing lies in calibration of the test systems. Typically, this is accomplished by manual adjustment of variable resistors or the like while operating upon test specimens of known hardness. Such calibration techniques are prone to error, due in part to the need for operator intervention and judgment, among other factors.

OBJECTS AND SUMMARY OF THE INVENTION

An object of the present invention is to provide a penetration hardness tester which alleviates or overcomes the aforementioned deficiencies in the art.

A more specific object of the invention is to provide a fully automated penetration hardness tester which performs penetration hardness tests on materials in less time than those previously proposed, and without any decrease in accuracy or repeatability.

Another object of the invention is to provide a penetration hardness tester which embodies facility for automatic calibration A further object of the invention is to provide a penetration hardness tester which may be used on both sides of a test specimen without decrease in accuracy or repeatability.

In accordance with one important aspect of the present invention, a penetration hardness tester is provided with a penetrator adapted to engage test specimens and structure for applying a plurality of loads in a predetermined sequence to the specimen through the penetrator so as to cause varying depth of penetration of the penetrator into the test specimen. Motion of the penetrator with respect to the test specimen is monitored for automatically initiating application (or removal) of the next load in the sequence when motion of the penetrator following application of the preceding load has terminated. Specimen hardness is indicated as a function of depth of penetration under the varying loads. In the preferred embodiment of the invention, motion of the penetrator is monitored and application of successive loads is initiated by sampling penetrator displacement at preselected intervals and initiating the next load cycle in the predetermined sequence when penetration displacement remains within a predetermined range for a preselected number of successive sampling intervals. Penetrator position for purposes of determining specimen hardness is determined as the average penetrator position within the range.

In accordance with another important aspect of the present invention, specimen hardness is determined as a linear function of a difference in penetrator depth of penetration under so-called minor load before and after application of the so-called major load, and a calibration system is provided for automatically setting gain and offset of such linear function. Specifically, apparent hardness readings are obtained and stored for two standard specimens of differing known hardnesses, and actual hardnesses are entered by an operator. Gain and offset of the linear function are then automatically determined by calibration circuitry from the actual and apparent hardness readings as a solution to two linear equations with two unknowns.

A further aspect of the invention contemplates provision of serially connected cylinders, preferably controlled pneumatic cylinders, for application of the sequence of loads to the specimen through the penetrator. A first cylinder has a piston coupled to the penetrator and a clamp collar affixed to the cylinder for engaging and holding a workpiece with respect to the penetrator. The second cylinder is disposed in fixed position and has a piston coupled to the first cylinder. Thus, energization of the second cylinder engages the clamping collar against the test specimen, while controlled energization of the first cylinder applies sequential load cycles to the clamped test specimen through the penetrator. An important feature of this structure is that the total force applied to the test specimen through the clamp collar and penetrator remains constant throughout the test cycle.

BRIEF DESCRIPTION OF THE DRAWINGS

The invention, together with additional objects, features and advantages thereof, will be best understood from the following description, the appended claims and the accompanying drawings in which:

FIG. 1 is a functional block diagram of a penetration hardness tester in accordance with a presently preferred embodiment of the invention;

FIG. 3 is a graph useful in understanding operation of the automatic calibration feature of the invention.

DETAILED DESCRIPTION OF PREFERRED EMBODIMENTS

Figure 2:
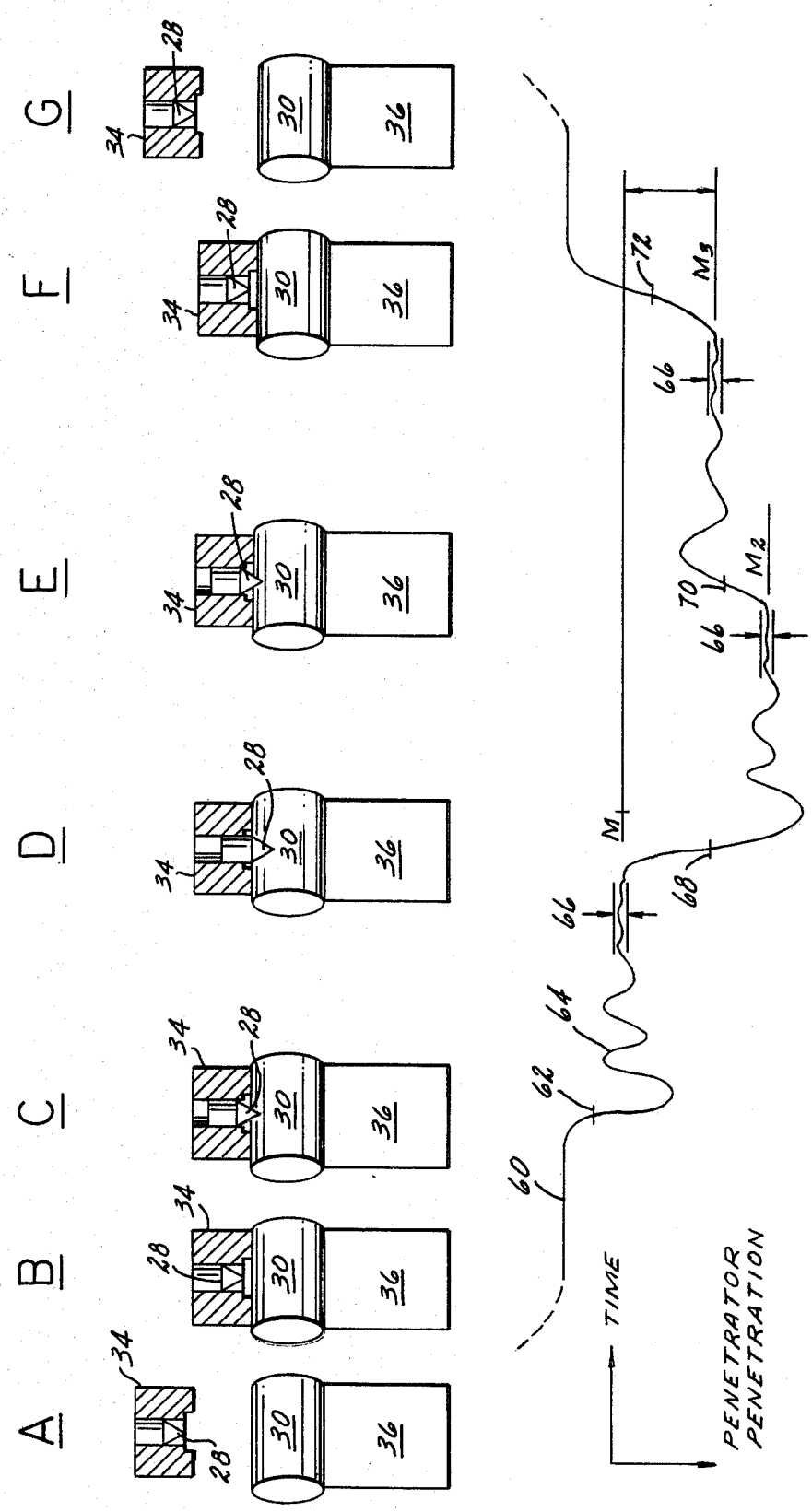
FIG. 2 is a schematic timing diagram illustrating operation of the invention through one test cycle.

The general theory of penetration hardness testing is well understood in the metallurgical arts. Generally, the standard test methods involve the use of ball- or diamond-tip penetrators, and major and minor loads of defined magnitudes. Specimen hardness is most often expressed in so-called Rockwell hardness numbers in one of a plurality of defined scales such as the C or B hardness scale, or the N superficial hardness scale. The Rockwell-type testing method is defined in detail in ASTM Publication E18-74. Rapid indentation hardness testing is defined in ASTM Publication E103-61. The background theory of penetration hardness testing need not be discussed herein except to the extent necessary to illustrate structure and operation of the present invention.

Referring to FIG. 1, a presently preferred embodiment 10 of a fully automatic penetration hardness tester in accordance with the present invention is illustrated therein as comprising a clamp head 12 which includes a pneumatic cylinder 14 held in fixed position and a piston 16 reciprocable therewithin. A power head 18 includes a movable pneumatic cylinder 20 coupled to the drive rod 22 of piston 16 and a piston 24 reciprocable within cylinder 20. The drive rod 26 of piston 24 is coupled to a penetrator 28 which is adapted to engage test specimens 30. A skirt 32 depends from cylinder 20 surrounding penetrator 28 and terminates in a clamp collar 34 which is adapted to engage and hold test specimen 30 against the specimen support 36. The position of penetrator 28 with respect to skirt 32 and clamp collar 34 is monitored by an LVDT generally indicated at 38.

LVDT 38 is connected through a differential amplifier 40 to the signal input of an analog-to-digital converter 42. The control input of converter 42 is received from a central control logic circuit 44, to which the output of converter 42 is directed. Control logic circuit 44 also directs load application control signals to the pressure regulators 46, which include suitable valves, etc. for applying and/or venting controlled air pressure to cylinders 14,20 of clamp head 12 and power head 18. Logic circuit 44 receives a control input from a start circuit 48, which may comprise suitable palm buttons or the like for manual initiation of a test cycle by an operator, or automatic machine-controlled start circuitry such as switches or sensors. Scale and mode select circuitry 50 feed outputs to control logic circuit 44 for selecting among hardness scales, such as the C, B and N scales previously described, and for operator selection of mode of operation, e.g. automated mode, calibration mode or manual mode. A data entry device 52 such as a keyboard is provided for feeding selected data to control logic circuit 44 during the calibration mode of operation, or for storage and later display during test cycles. Control logic 44 includes suitable circuitry for computing specimen hardness in the manner to be described, and for feeding such hardness readings to a suitable display 54 such as an LED display or the like. Specimen hardness and other data may also be fed to a computer or printer if desired.

FIG. 2 illustrates operation of penetration hardness tester 10 over one complete test cycle. The upper illustration in FIG. 2 illustrate positions of penetrator 28 and clamp collar 34 with respect to test specimen 30 and specimen support 36 at successive sequence stages A–G during one cycle of operation, and the lower illustration is a graph of depth of penetration versus time. The time scales of the upper and lower illustrations coincide, but otherwise the illustrations of FIG. 2 are not to scale.

Initially, at stage A, clamp collar 34 and penetrator 28 are spaced from test specimen 30. (This is also the stage of operation illustrated in FIG. 1.) A test cycle is initiated by start control 48 (FIG. 1), either manually or automatically by suitable part detection sensors or switches. Clamp head 12 is then energized at stage B by control logic 44 and pressure regulators 46 so as to lower clamp collar 34 under pressure to engage test specimen 30 and hold the same firmly against specimen support 36. Penetrator 28 follows collar 34 during this clamping operation, but does not engage the test specimen. After clamp 34 engages test specimen 30, the penetrator position 60 is read by control logic 44, and a first penetration threshold 62 with respect to position 60 is automatically set. With test specimen 30 clamped by collar 34, power head 18 is then automatically energized by control logic 44 and pressure regulators 46 to apply the minor load to the test specimen through penetrator 28. For hardness testing in the Rockwell C scale, for example, the minor load would be 10 kilograms in accordance with ASTM specifications.

Penetrator 28 enters test specimen 30 during stage C under application of the minor load. When the depth of penetration monitored by LVDT 38 exceeds previously-set threshold 62, control logic circuit 44 begins sampling penetrator position through amplifier 40 and A/D converter 42, and storing such position readings within internal control logic memory. This sampling and storing operation continues at predetermined intervals. After the minor load has been fully applied, penetrator position begins settling in a decaying oscillatory manner as illustrated at 64 toward its final position under minor load. Control logic circuit 44 continues to sample and store penetrator positions during this settling time. When a predetermined number of successive position readings fall within a preselected position range 66, control logic 44 extrapolates the final penetrator position as the average position indicated by this predetermined number of readings. This average position is indicated at M1 in FIG. 2. At the same time, control logic 44 computes a second penetration threshold 68 deeper than position M1, senses completion of the first minor load cycle, and at stage D applies the major load to penetrator 28 through pressure regulators 46 and power head 18. For Rockwell C hardness testing, the major load would be 150 kg.

As the penetrator penetrates the test specimen under application of major load during stage D and the depth of penetration exceeds threshold 68, control logic 44 again samples and stores successive penetrator position readings until the predetermined number of readings again falls within range 66. Such condition is interpreted as indicating completion of the major load cycle, and penetrator position M2 under major load is computed as the average of the successive readings which fall within range 66. Again, a third threshold 70 is computed with respect to position M2 and stage E is initiated by removing the major load. Resiliency of the test specimen causes the penetrator to move out of the workpiece even though the minor load is still applied, and when penetrator position passes threshold 70, control logic 44 again samples and stores readings indicative of penetrator position. When the predetermined number of successive readings again falls within range 66, penetrator position M3 is extrapolated as the average thereof, and a fourth threshold 72 is computed. The minor load is then removed to initiate stage F, and when penetrator position passes threshold 72, completion of a test cycle is indicated. Control logic 44 then operates at stage G through pressure regulators 46 and clamp head 12 to remove clamp collar 34 from test specimen 30.

It will be appreciated, of course, that the thresholds 62, 68, 70 and 72 are essentially arbitrary and are used for control purposes only. That is, failure to reach a threshold during a corresponding cycle of operation would indicate malfunction and lead to an abort sequence or indication. Both the thresholds 68, 70, 72 and the range 66 "float" in the sense that they are not associated with or set at predetermined penetration depths. Stated differently, range 66 may be thought of as a floating window which follows penetrator position. When a predetermined number of successive position readings fall within this range or window, control logic interprets this as indicating that penetrator motion has "settled" sufficiently to permit accurate extrapolation of final position, preferably as an average of the position readings within range 66. The next stage of operation may then be initiated without extended time delays.

In a working embodiment of the present invention, control logic circuit 44 functions to sample penetrator position at intervals of 100 microseconds and the range 66 employed for identifying termination of successive load cycles is equal to 32 millionths of an inch. When ten successive position readings fall within the range of 16 millionths of an inch, termination of the particular load cycle is indicated as previously described, and penetrator position M1, M2 or M3 is computed as the average of these ten readings. It will be appreciated, of course, that the sampling intervals must be empirically selected to ensure that successive readings within range 66 actually indicate penetrator settling. Likewise, range 66 may vary for differing materials or hardness scales. The position displacements associated with thresholds 62, 68, 70 and 72 may likewise vary with hardness scale.

With the readings M1, M2 and M3 thus obtained, Rockwell hardness may be determined in the usual manner. For example, it is conventional to determine Rockwell-C hardness $R_{HC}$ in accordance with linear equation $$R_{HC} = 100 - \frac{K(M3 - M1)}{.00008 \text{ inch}} \quad (1)$$

wherein M3 and M1 are the minor load readings previously described measured in inches, and K is a constant which varies with selected hardness scale. As with any non-ideal linear system, sources of repeatable error must be calibrated into the computation system, so that the equation for computation of Rockwell hardness for the system of FIG. 1 will be $$R_{HC} = a \left[ 100 - \left( \frac{K(M3 - M1)}{.00008 \text{ inch}} \right) \right] + b \quad (2)$$

wherein gain a and offset b are constants related to sources of repeatable errors in the measuring system, such as the angle of diamond penetrator 28, variations in major and minor loads due to misadjustment of pressure regulators 46, and computation circuit constants. In accordance with another important feature of the present invention, gain a and offset b are automatically calibrated by control logic 44, and this calibration technique is illustrated in FIG. 3.

Specifically, when calibration is called for, such as when penetrator 28 is changed or the system is initially energized, the operator enters the calibration mode of operation through mode select circuitry 50. A test specimen of known hardness RHH is placed beneath the penetrator 28 and actual known hardness is entered through data entry circuitry 52. A test sequence is then manually initiated by means of start circuitry 48, and control logic 34 obtains and displays a corresponding measured or apparent hardness reading RHH'. The operator then removes test specimen RHH and inserts a specimen RHS of known differing hardness. Actual hardness is again entered through data entry circuit 52, and a test sequence is initiated through start circuit 48. Control logic 44 again determines and displays a corresponding measured or apparent hardness RHS'. (Apparent hardness readings RHH' and RHS' may be the average of several readings.) Control logic 44 then solves the equations $$RHH = a\ RHH' + b \quad (3)$$

$$RHS = a\ RHS' + b \quad (4)$$

for the "unknowns" a and b, and the calibration operation is completed.

In the working embodiment of the invention previously described, control logic circuit 44 comprises a Motorola 6809 microprocessor. Attached hereto as Apendix A is a complete software listing in SPL/M and assembly language for programming such microprocessor to function in accordance with the present invention as previously described. The automatic sequencing features of the present invention hereinabove discussed in detail with reference to FIG. 2 are implemented by instructions extending from pages A-32, line 125 to A-35, line 281. The automatic calibration technique of the present invention hereinabove discussed in detail with reference to FIG. 3 is implemented by instructions extending from page A-19, line 853 to page A-20, line 870, page A-23, line 1048 to page A-27, line 1255 and page A-33, line 208 to page A-35, line 294. The remaining instructions in the Appendix are directed to functions not pertinent to the subject matter of the present application. It will be readily apparent to person having ordinary skill in the art that other microprocessors and/or programming may be readily devised and employed embodying the principles and features of the present invention. Indeed, control logic circuit 44 may be comprised of suitable discrete solid state logic circuitry constructed and arranged to operate as described.

Thus, it will be appreciated that the embodiment of the invention hereinabove described in detail fully satisfies all of the objects and aims previously set forth. For example, actual hardness testing is fully automatic and does not require any intervention or interpretation by an operator. The testing sequence may be initiated manually using start circuit 48 during the calibration mode of operation, and in fact the entire tester 10 may be disposed exclusively for such manual initiation as in a test laboratory or the like. However, the invention finds particular utility and application in the environment of an automated manufacturing or test process wherein the test specimen support 36 comprises a suitable specimen conveyor, and start circuit 48 comprises suitable sensors for determining when a test specimen 30 is disposed beneath penetrator 28 and clamp 34. Indeed, a particularly important feature of the present invention which finds application in such automated environment resides in that feature whereby control logic circuit 44 identifies termination of each load sequence by monitoring penetrator position and proceeds to the next load cycle when a number of successive penetrator position readings fall within range 66 (FIG. 2). This feature may be distinguished from prior art automated testing techniques wherein a delay circuit or timer suspends operation for a preset time after application (or removal) of each load. Thus, whereas such time-delayed testing may require on the order of ten seconds complete a test cycle, the same cycle may be completed in less than 2.5 seconds in accordance with the present invention without significant loss of accuracy or repeatability. As previously noted, penetrator settling time varies with hardness of the test specimen. Thus, settling time at each position M1, M2, M3 in FIG. 2 will be substantially longer for a soft part than for a hard part. The present invention functions to obtain the fastest test cycle time for each part under test.

Another important feature of the invention resides in the fact that total pressure applied to the test specimen by clamp 34 and penetrator 28 remains constant throughout the test sequence. Penetrator position is referenced to the clamp which engages the penetrated surface of the test specimen, and thus to the upper surface of the test piece, so that errors caused by dust, oil or scale, etc. under the test pieces, i.e. between test piece 30 and support 36, are eliminated. Indeed, whereas conventional hardness testers may not be used on both sides of a test block due to the crater-effect caused by testing on one side, the tester of the present invention may be employed on both sides of a test block because the "craters" on the bottom side are compressed by initial application of clamping force (stage B in FIG. 2) and remain compressed to the same extent throughout the test cycle because the total force applied by the clamp and penetrator remains constant.

The invention can be used for rapid indentation hardness testing, as described by the American National Standard ASTME 103-61. A modification of the invention contemplates measurement of specimen hardness as a function of depth of penetration between major and minor loads - i.e. as a function of M2—M1 in FIG. 2.

The invention claimed is:

1. An automatic penetration hardness tester comprising a penetrator adapted to engage test specimens, means for applying a plurality of loads in a predetermined sequence to a test specimen through said penetrator so as to cause varying penetration depth of said penetrator into the test specimen, means responsive to motion of said penetrator with respect to the test specimen for automatically initiating application of the next load in said sequence when motion of said penetrator following application of the preceding load in said sequence has terminated, and means responsive to depth of penetration under said plurality of loads for indicating specimen hardness.

2. The tester set forth in claim 1 wherein said motion-responsive means comprises means for establishing a range of displacement of said penetrator and means responsive to absence of displacement out of said range to indicate termination of motion of said penetrator.

3. The tester set forth in claim 2 wherein said displacement-responsive means is responsive to absence of displacement out of said range for a predetermined time period to indicate said termination of motion.

4. The tester set forth in claim 3 wherein said displacement-responsive means comprises means for sampling penetrator displacement at predetermined time intervals and means for indicating said termination of motion when sampled displacement remains within said range for a preselected number of successive intervals.

5. The tester set forth in claim 1 wherein said means for applying said plurality of loads comprises pneumatic cylinder means coupled to said penetrator.

6. The tester set forth in claim 5 wherein said means for applying said plurality of loads further comprises means for selecting among a plurality of standard hardness scales, and means for energizing said pneumatic cylinder means to apply predetermined loads to the specimen through said penetrator which vary as a function of selected hardness scale.

7. The tester set forth in claim 5 wherein said pneumatic cylinder means comprises a first head including a first pneumatic cylinder having a piston coupled to said penetrator and clamp means affixed to said first cylinder for engaging and holding a workpiece with respect to said penetrator, a second head including a fixed second pneumatic cylinder and a second piston coupled to said first cylinder, means for energizing said second head in a first sequence of operation for clamping a test specimen with respect to said penetrator and means for energizing said second head in a second sequence of operation for applying said plurality of loads to the test specimen through said penetrator, the total force applied to the test specimen through said clamp means and said penetrator remaining constant throughout said first and second sequences of operation.

8. The tester set forth in claim 7 wherein said motion-responsive means comprises means for monitoring motion of said penetrator with respect to said clamp means, such that said motion-responsive means is responsive to motion of said penetrator with respect to that portion of the test specimen engaged by said clamp means.

9. The tester set forth in claim 1 wherein said means for applying said plurality of loads comprises means for applying a first load to a test specimen through said penetrator, means for then applying a second load in addition to said first load to the specimen through said penetrator, and means for then removing said second load while maintaining said first load on the specimen through said penetrator, and wherein said depth of penetration-responsive means comprises means responsive to a difference in penetration under said first load before and after application of said second load for indicating material hardness.

10. The tester set forth in claim 9 wherein said difference-responsive means is adapted to indicate material hardness as a linear function of said difference.

11. The tester set forth in claim 10 further comprising means for calibrating said difference-responsive means for gain and offset of said linear function, including means for obtaining and storing apparent hardness readings indicated by said difference responsive means for two specimens of differing known hardnesses, and means for automatically setting said gain and offset as a combined function of said apparent and known hardnesses.

12. An automatic penetration hardness tester comprising a penetrator adapted to engage test specimens, means for selectively applying first and second loads to a test specimen through said penetrator in the load cycle sequence: first load, first load plus second load, first load, so as to cause varying depth of penetration of said penetrator into the test specimen as a function of each said load cycle, means responsive to motion of said penetrator into and out of the test specimen for automatically initiating application of the next load cycle in said sequence when motion of said penetrator following application of the preceding load cycle in said sequence has terminated, and means responsive to depth of penetration under said first load before and after application of said second load for indicating material hardness.

13. The tester set forth in claim 12 wherein said motion-responsive means comprises means for establishing a predetermined range of displacement of said penetrator and means responsive to absence of displacement of said penetrator out of said range for a predetermined time period following application of each said load cycle for initiating application of the next said load 14. The testor set forth in claim 13 wherein said means responsive to depth of penetration includes means for determining depth of penetration under each said load cycle as a function of average position of said penetrator within said range over said time period.

15. A penetration hardness tester comprising a penetrator adapted to engage test specimens, means for applying a plurality of loads to a test specimen through said penetrator, means for monitoring depth of penetration of said penetrator into a test specimen under said plurality of loads, means for indicating material hardness of the test specimen as a linear function of penetration under said varying loads, and means for calibrating said indicating means for gain and offset of said linear function comprising means for obtaining and storing apparent hardness readings indicated by said indicating means for two specimens of differing known hardnesses, and means for automatically setting said gain and offset of said linear function within said indicating means as a function of said apparent and known hardnesses.

16. A penetration hardness tester comprising a penetrator adapted to engage a test specimen, a first head including a first cylinder having a piston coupled to said penetrator and clamp means affixed to said first cylinder for engaging and holding a workpiece with respect to said penetrator, a second head having a fixed cylinder and a second piston coupled to said first head, means for monitoring position of said penetrator with respect to said first cylinder and said clamping means, means for energizing said second head in a first sequence of operation for clamping a test specimen with respect to said penetrator, means for energizing said first head in a second sequence of operation for applying a plurality of loads in a predetermined sequence to the clamped test specimen through said penetrator, the total force applied to the test specimen through said clamp means and said penetrator remaining constant throughout said first and second sequences of operation, means responsive to said position-monitoring means for energizing said first and second heads in said first and second sequences of operation and applying said plurality of loads in said predetermined sequence, and means responsive to depth of penetration of said penetrator into a test specimen under said plurality of loads in said second sequence of operation for indicating hardness of the test specimen.

17. The tester set forth in claim 16 wherein said means responsive to said position-monitoring means comprises means for establishing a predetermined range of displacement of said penetrator and means responsive to absence of displacement of said penetrator out of said range for a predetermined time period following application of each said load during said second sequence of operation for automatically initiating application of the next load in said sequence.

\* \* \* \* \*